United States Patent
Fu

(10) Patent No.: US 7,291,738 B2
(45) Date of Patent: Nov. 6, 2007

(54) THERAPEUTIC COMPOUNDS

(75) Inventor: Jian-Min Fu, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 103 days.

(21) Appl. No.: 10/375,687

(22) Filed: Feb. 27, 2003

(65) Prior Publication Data

US 2003/0181485 A1   Sep. 25, 2003

(51) Int. Cl.
    *C07D 215/38* (2006.01)
(52) U.S. Cl. .................. 546/169; 544/364; 540/580; 540/607
(58) Field of Classification Search ............... 544/364; 546/169; 540/580, 607; 514/215, 314, 217.04, 514/253.01
    See application file for complete search history.

(56) References Cited

FOREIGN PATENT DOCUMENTS

WO   WO 97/46899   12/1997
WO   WO 97/48700   12/1997

OTHER PUBLICATIONS

Bromidge, MS et al '1-[2-[(Heteroaryloxy)heteroaryl]carbamoyl]indolines: novel and selective 5-HT2C receptor inverse agonis with potential as antidepressant/Anxiolytic agents' CA 133:275848 (2000).*

Bromidge etal CA 133:275848.*

1-[2-[(Heteroaryloxy)heteroaryl]carbamoyl]indolines: Novel and Selective 5-HT$_{2c}$ Receptor Inverse Agonists with Potential as Antidepressant/Anxiolytic Agents, by S.M. Bromidge, et al, Bioorganic & Medicinal Chemistry Letters 10 (2000) 1863-1866.

* cited by examiner

*Primary Examiner*—Janet L. Andres
*Assistant Examiner*—David E Gallis

(57) ABSTRACT

The present invention provides compounds, for example, of formula (I):

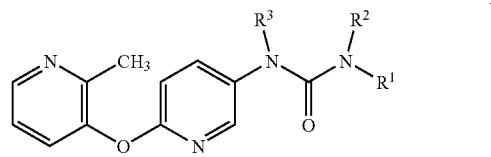

wherein $R^1$, $R^2$, and $R^3$ have any of the values defined in the specification, as well as pharmaceutical compositions comprising the compounds. The invention also provides therapeutic methods, and processes and intermediates useful for preparing compounds of formula I.

2 Claims, No Drawings

THERAPEUTIC COMPOUNDS

FIELD OF THE INVENTION

The present invention provides urea compounds of formula (I) as described herein below. These compounds and pharmaceutically acceptable salts thereof, are serotonin receptor ligands useful for treating a variety of diseases and conditions related to 5-HT receptor activity.

BACKGROUND OF THE INVENTION

Serotonin has been implicated in a number of diseases and conditions that originate in the central nervous system. These include diseases and conditions related to sleeping, eating, perceiving pain, controlling body temperature, controlling blood pressure, depression, anxiety, schizophrenia, and other bodily states. R. W. Fuller, Biology of Serotonergic Transmission, ed. Neville V. Osborne, John Wiley and Sons (1982), p 221; D. J. Boullin, Serotonin in Mental Abnormalities 1, John Wiley and Sons (1978), p. 316; J. Barchas, et al., Serotonin and Behavior, Academic Press, New York, N.Y. (1973); Barnes, N. M.; A Review Of Central 5-HT Receptors And Their Function, *Neuropharmacology*, 38, (1999), 1083-1152. Serotonin also plays an important role in peripheral systems, such as the gastrointestinal system, where it has been found to mediate a variety of contractile, secretory, and electrophysiologic effects.

As a result of the broad distribution of serotonin within the body, there is a tremendous interest in drugs that affect serotonergic systems. In particular, receptor-specific agonists and antagonists are of interest for the treatment of a wide range of disorders, including anxiety, depression, hypertension, migraine, obesity, compulsive disorders, schizophrenia, autism, neurodegenerative disorders, for example, Alzheimer's disease, Parkinsonism, and Huntington's chorea, and chemotherapy-induced vomiting. M. D. Gershon, et al., The Peripheral Actions of 5-Hydroxytryptamine, 246 (1989); P. R. Saxena, et al., *Journal of Cardiovascular Pharmacology*, 15:Supplement 7 (1990).

The major classes of serotonin receptors ($5\text{-}HT_{1-7}$) contain fourteen to eighteen separate receptors that have been formally classified. See Glennon, et al., *Neuroscience and Behavioral Reviews*, 1990, 14, 35; and D. Hoyer, et al. *Pharmacol. Rev.* 1994, 46, 157-203. Recently discovered information regarding subtype identity, distribution, structure, and function suggests that it is possible to identify novel, subtype specific agents, having improved therapeutic profiles, for example, fewer side effects.

For example, the $5\text{-}HT_2$ family of receptors is comprised of $5\text{-}HT_{2A}$, $5\text{-}HT_{2B}$, and $5\text{-}HT_{2C}$ subtypes, which have been grouped together on the basis of primary structure, secondary messenger system, and operational profile. All three subtypes are G-protein coupled, activate phospholipase C as a principal transduction mechanism, and contain a seven-transmembrane domain structure. There are distinct differences in the distribution of the three $5\text{-}HT_2$ subtypes. The $5\text{-}HT_{2B}$ and $5\text{-}HT_{2A}$ receptors are widely distributed in the periphery, while the $5\text{-}HT_{2C}$ receptor has been found only in the central nervous system, being highly expressed in many regions of the human brain. See G. Baxter, et al., *Trends in Pharmacol. Sci.*, 1995, 16, 105-110.

Subtype $5\text{-}HT_{2A}$ has been associated with effects including vasoconstriction, platelet aggregation, and bronchoconstriction, while subtype $5\text{-}HT_{2C}$ has been associated with diseases that include depression, anxiety, obsessive compulsive disorder, panic disorders, phobias, psychiatric syndromes, and obesity. Very little is known about the pharmacologic role of the $5\text{-}HT_{2B}$ receptor. See F. Jenck, et al., *Exp. Opin. Invest. Drugs*, 1998, 7, 1587-1599; M. Bos, et al., *J. Med. Chem.*, 1997, 40, 2762-2769; J. R. Martin, et al., *The Journal of Pharmacology and Experimental Therapeutics*, 1998, 286, 913-924; S. M. Bromidge, et al., *J. Med. Chem.*, 1998, 41 1598-1612; G. A. Kennett, *IDrugs*, 1998, 1, 456-470; and A. Dekeyne, et al., *Neuropharmacology*, 1999, 38, 415-423; Isaac, M., *Drugs of the Future*, 2001, 26, 383-393.

INFORMATION DISCLOSURE

International Patent Application Publication Number WO 97/48699 discloses compounds of the general formula:

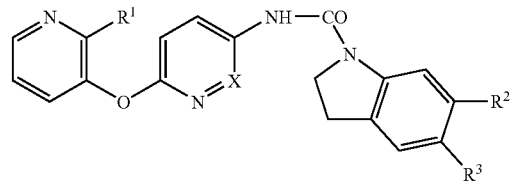

useful in the treatment of CNS disorders such as anxiety.

International Patent Application Publication Number WO 97/48700 discloses compounds of the general formula

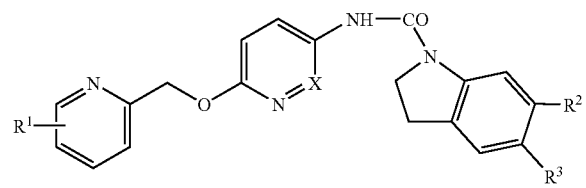

useful in the treatment of CNS disorders such as anxiety.

In spite of the above reports, there is currently a need for pharmaceutical agents that are useful to treat diseases and conditions associated with 5-HT receptors.

SUMMARY OF THE INVENTION

In accordance with the present invention, novel compounds which demonstrate useful biological activity, and particularly activity as 5-HT receptor ligands, are provided. Thus, the present invention provides [6-(2-methyl-pyridin-3-yloxy)pyridin-3-yl] ureas of formula (I):

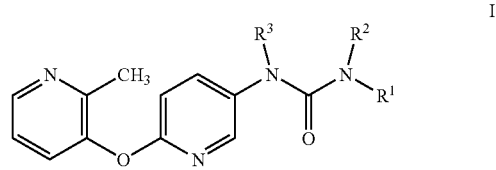

wherein $R^1$ is aryl, substituted aryl, aryl($C_{1-8}$alkylene), substituted aryl($C_{1-8}$alkylene), heteroaryl, substituted heteroaryl, heteroaryl($C_{1-8}$alkylene), substituted heteroaryl($C_{1-8}$alkylene), heterocycle, substituted heterocycle, heterocycle($C_{1-8}$alkylene), or substituted heterocycle($C_{1-8}$alkylene), and $R^2$ and $R^3$ are each independently H, $C_{1-8}$alkyl, aryl($C_{1-8}$alkylene) and substituted aryl($C_{1-8}$alkylene);

or $R^1$ and $R^2$ together with the nitrogen to which they are attached form a heterocycle, substituted heterocycle, heteroaryl, or substituted heteroaryl, and $R^3$ is H, $C_{1-8}$alkyl, aryl($C_{1-8}$alkylene) or substituted aryl($C_{1-8}$alkylene);

or a pharmaceutically acceptable salt thereof;

provided $R^1$ and $R^2$ together with the nitrogen to which they are attached are not 2,3-dihydroindol-1-yl, or substituted 2,3-dihydroindol-1-yl; and provided that $R^1$ and $R^2$ together with the nitrogen to which they are attached are not 2,3,4,5-tetrahydro-1H-benzo[d]azepin-1-yl, or substituted 2,3,4,5-tetrahydro-1H-benzo[d]azepin-1-yl.

In another aspect, the present invention also provides:

a pharmaceutical composition comprising a compound of formula (I), or a pharmaceutically acceptable salt thereof, and a pharmaceutically acceptable excipient, the composition preferably comprises a therapeutically effective amount of the compound or salt;

a method for treating a disease or condition in a mammal, for example, a human, wherein a 5-HT receptor is implicated and modulation of a 5-HT function is desired comprising administering a therapeutically effective amount of a compound of formula (I), or a pharmaceutically acceptable salt thereof to the mammal;

a method for treating or preventing a disease or disorder of the central nervous system in a mammal comprising administering a therapeutically effective amount of a compound of formula (I), or a pharmaceutically acceptable salt thereof to the mammal;

a compound of formula (I) or a pharmaceutically acceptable salt thereof for use in medical diagnosis or therapy, for example, the treatment or prevention of 5-HT related disease such as anxiety, obesity, depression, or a stress-related disease;

the use of a compound of formula (I), or a pharmaceutically acceptable salt thereof to prepare a medicament useful for treating or preventing a disease or disorder of the central nervous system in a mammal; or a method for modulating 5-HT receptor function, comprising administering an effective modulatory amount of a compound of formula (I), or a pharmaceutically acceptable salt thereof.

The invention also provides synthetic intermediates and processes disclosed herein that are useful for preparing compounds of formula (I).

Compounds of formula (I) are 5-HT ligands. Thus, radiolabeled compounds of formula (I) are useful as imaging agents and biomarker for medical therapy and diagnosis. Such radiolabeled compounds are also useful as pharmacological tools for studying 5-HT function and activity. Accordingly, the invention also provides a radiolabeled compound of formula (I), or a salt thereof.

The invention also provides a radiolabeled compound of formula (I) for use in medical diagnosis or therapy, as well as the use of a radiolabeled compound of formula (I) to prepare a medicament useful for medical diagnosis or therapy.

The present invention further provides a method of performing positron emission tomography comprising incorporating an isotopically labeled compound of formula I or a pharmaceutically acceptable salt thereof into tissue of a mammal and detecting the compound distributed into said tissue.

The present invention further provides a method of performing nuclear magnetic resonance imaging comprising:

incorporating an isotopically labeled compound of formula I or a pharmaceutically acceptable salt thereof into tissue of a mammal and detecting the compound distributed in said tissue.

The present invention further provides a method of performing single photon emission computed tomography comprising incorporating an isotopically labeled compound of formula I or a pharmaceutically acceptable salt thereof into tissue of a mammal and detecting the compound distributed into said tissue.

The present invention further provides the use of a compound of formula I or a pharmaceutically acceptable salt thereof to prepare a medicament for treating or preventing diseases or disorders of the central nervous system.

Further aspects and embodiments of the invention may become apparent to those skilled in the art from a review of the following detailed description, taken in conjunction with the examples and the appended claims. While the invention is susceptible of embodiments in various forms, described hereafter are specific embodiments of the invention with the understanding that the present disclosure is intended as illustrative, and is not intended to limit the invention to the specific embodiments described herein.

DETAILED DESCRIPTION OF THE INVENTION

The compounds of the invention are useful for treating or preventing diseases or disorders of the central nervous system. Specific diseases or disorders of the central nervous system for which a compound of formula (I) may have activity include, but are not limited to: obesity; depression; schizophrenia; schizophreniform disorder; schizoaffective disorder; delusional disorder; a stress-related disease, for example, general anxiety disorder, panic disorder, a phobia, obsessive compulsive disorder, post-traumatic-stress syndrome, immune system depression; a stress-induced problem with the urinary; gastrointestinal or cardiovascular system, for example, stress incontinence; neurodegenerative disorders; autism; chemotherapy-induced vomiting; hypertension; migraine; headaches; cluster headaches; sexual dysfunction in a mammal, for example, a human; addictive disorder and withdrawal syndrome; an adjustment disorder; an age-associated learning and mental disorder; anorexia nervosa; apathy; an attention-deficit disorder due to general medical conditions; attention-deficit hyperactivity disorder; behavioral disturbance, including agitation in conditions associated with diminished cognition, for example, dementia, mental retardation or delirium; bipolar disorder; bulimia nervosa; chronic fatigue syndrome; conduct disorder; cyclothymic disorder; dysthymic disorder; fibromyalgia and other somatoform disorders; generalized anxiety disorder; an inhalation disorder; an intoxication disorder; movement disorder, for example, Huntington's disease or Tardive Dyskinesia; oppositional defiant disorder; peripheral neuropathy; premenstrual dysphoric disorder; a psychotic disorder (brief and long duration disorders, psychotic disorder due to medical condition, psychotic disorder NOS); mood disorder (major depressive or bipolar disorder with psychotic features); seasonal affective disorder; a sleep disorder; a specific development disorder; agitation disorder; selective serotonin reuptake inhibition (SSRI) "poop out" syndrome; or a Tic disorder, for example, Tourette's syndrome.

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. The term "alkylene" refers to a divalent straight or branched hydrocarbon chain (e.g. ethylene —$CH_2CH_2$—). The term "aryl$C_{1-8}$alkylene" for example includes benzyl, phenethyl, naphthylmethyl and the like.

"Aryl" denotes a phenyl radical or an ortho-fused bicyclic carbocyclic radical having about eight to ten ring atoms in which at least one ring is aromatic. Examples of aryl include phenyl, naphthyl, and indenyl.

"Heteroaryl" denotes a radical of a monocyclic aromatic ring containing five or six ring atoms consisting of carbon and 1, 2, 3, or 4 heteroatoms each independently selected from the group consisting of non-peroxide oxygen, sulfur, and N(W) wherein W is absent or is H, O, $C_{1-4}$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl groups include, but are not limited to, 2H-pyrrolyl, 3H-indolyl, 4H-quinolizinyl, 4H-carbazolyl, acridinyl, benzo[b]thienyl, benzothiazolyl, β-carbolinyl, carbazolyl, chromenyl, cinnaolinyl, furazanyl, furyl, imidazolyl, imidizolyl, indazolyl, indolisinyl, indolyl, isobenzofuranyl, isoindolyl, isoquinolyl, isothiazolyl, isothiazolyl, isoxazolyl, isoxazolyl, naphthyridinyl, naptho [2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridinyl, pyrimidinyl, pyrimidinyl, pyrrolyl, quinazolinyl, quinolyl, quinoxalinyl, thiadiazolyl, thianthrenyl, thiazolyl, thienyl, triazolyl, xanthenyl, and the like. The heteroaryl attaches not only at any carbon atom of sufficient valency but also at any heteroatom of sufficient valency that can form a stable compound.

"Heterocycle" includes monocyclic, polycyclic, and bridged ring systems, which can be saturated or partially unsaturated, containing one or more non-aromatic rings, such as 2, 3, or 4, and containing at least one nitrogen, oxygen, or sulfur atom in any of the non-aromatic rings. Examples of heterocyclic groups include, but are not limited to, monocyclic, bicyclic, or tricyclic groups which groups contain one or more heteroatoms and from about 3 to about 20 total ring atoms. The term "heterocycle" also includes such ring systems that include one to three benzo rings fused thereto. Examples of heterocycle include heterocycles can be, for example, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

"Substituted aryl" includes an aryl group as described herein which is substituted with one or more (e.g. 1, 2, 3, or 4) substituents independently selected from nitro, $N_3$, $C_{1-8}$alkyl, $C_{1-8}$alkoxy, cyano, $OCF_3$, $CF_3$, halo, hydroxy, —$S(O)_{0-2}C_{1-8}$alkyl, $C_{1-8}$alkanoyl, $C_{1-8}$alkanoyloxy, —$NR_cR_d$, —$C(\!=\!O)NR_cR_d$, —$C(\!=\!S)NR_cR_d$, and —$SO_2NR_cR_d$, wherein $R_c$ and $R_d$ are each independently hydrogen, $C_{1-8}$alkyl, $C_{1-8}$alkanoyl, $C_{1-8}$alkoxycarbonyl, aryl, aryl($C_{1-8}$alkylene), heteroaryl, heteroaryl($C_{1-8}$alkylene), heterocycle, or heterocycle($C_{1-8}$alkylene), or $R_c$ and $R_d$ together with the nitrogen to which they are attached form a pyrrolidino, piperidino, morpholino, or thiomorpholino ring.

"Substituted heteroaryl" includes a heteroaryl group as described herein which is substituted with one or more (e.g. 1, 2, 3, or 4) substituents independently selected from nitro, $N_3$, $C_{1-8}$alkyl, $C_{1-8}$alkoxy, cyano, $OCF_3$, $CF_3$, halo, hydroxy, —$S(O)_{0-2}C_{1-8}$alkyl, $C_{1-8}$alkanoyl, $C_{1-8}$alkanoyloxy, —$NR_cR_d$, —$C(\!=\!O)NR_cR_d$, —$C(\!=\!S)NR_cR_d$ and —$SO_2NR_cR_d$, wherein $R_c$ and $R_d$ are each independently hydrogen, $C_{1-8}$alkyl, $C_{1-8}$alkanoyl, $C_{1-8}$alkoxycarbonyl, aryl, aryl($C_{1-8}$alkylene), heteroaryl, heteroaryl($C_{1-8}$alkylene), heterocycle, or heterocycle($C_{1-8}$alkylene), or $R_c$ and $R_d$ together with the nitrogen to which they are attached form a pyrrolidino, piperidino, morpholino, or thiomorpholino ring.

"Substituted heterocycle" includes a heterocycle as described herein which is substituted with one or more (e.g. 1, 2, 3, or 4) substituents independently selected from nitro, $C_{1-8}$alkyl, $C_{1-8}$alkoxy, cyano, $N_3$, $OCF_3$, $CF_3$, halo, hydroxy, —$S(O)_{0-2}C_{1-8}$alkyl, $C_{1-8}$alkanoyl, $C_{1-8}$alkanoyloxy, —$NR_cR_d$, —$C(\!=\!O)NR_cR_d$, —$C(\!=\!S)NR_cR_d$, —$SO_2NR_cR_d$, and oxo (=O), wherein $R_c$ and $R_d$ are each independently hydrogen, $C_{1-8}$alkyl, $C_{1-8}$alkanoyl, $C_{1-8}$alkoxycarbonyl, aryl, aryl($C_{1-8}$alkylene), heteroaryl, heteroaryl($C_{1-8}$alkylene), heterocycle, or heterocycle($C_{1-8}$alkylene), or $R_c$ and $R_d$ together with the nitrogen to which they are attached form a pyrrolidino, piperidino, morpholino, or thiomorpholino ring.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms, for example, by resolution of the racemic form by recrystallization techniques, by synthesis from optically-active starting materials, by chiral synthesis, or by chromatographic separation using a chiral stationary phase, and how to determine 5-HT activity using the standard tests which are well known in the art.

The carbon atom content of various hydrocarbon-containing moieties is indicated by a prefix designating the minimum and maximum number of carbon atoms in the moiety, that is, the prefix $C_{i-j}$ indicates a moiety of the integer "i" to the integer "j" carbon atoms, inclusive. Thus, for example, $C_{1-8}$alkyl refers to alkyl of one to eight carbon atoms, inclusive.

The compounds of the present invention are generally named according to the IUPAC or CAS nomenclature system. Abbreviations which are well known to one of ordinary skill in the art may be used, for example, "Ph" for phenyl, "Me" for methyl, "Et" for ethyl, "h" for hour or hours and "rt" for room temperature. DMF refers to N,N-dimethylformamide.

To the extent that any numerical range is recited in connection with any aspect of the inventive compounds, for example, dosages, treatment regimens, and the like, the range expressly includes all numerals, integer and fractional, falling within the range.

Specific and preferred values listed below for radicals, substituents, and ranges, are for illustration only; they do not exclude other defined values or other values within defined ranges.

Specifically, $C_{1-8}$ alkyl can be, for example, methyl, ethyl, propyl, isopropyl, butyl, iso-butyl, sec-butyl, pentyl, 3-pentyl, hexyl, heptyl or octyl; $C_{1-8}$alkylene can be methylene, 1,2-ethanediyl, 1,3-propanediyl, 1,2-isopropanediyl, 1,4-butanediyl, 1,2-butanediyl, 1,3-iso-butanediyl, 1,2-sec-butanediyl, 1,5-pentanediyl, 1,6-hexanediyl, 1,7-heptanediyl, or 1,8-octanediyl; $C_{1-8}$alkoxy can be methoxy, ethoxy, propoxy, isopropoxy, butoxy, iso-butoxy, sec-butoxy, pentoxy, 3-pentoxy, hexyloxy, heptyloxy, or octyloxy; $C_{1-8}$alkanoyl can be acetyl, propanoyl, butanoyl, pentanoyl, 4-methylpentanoyl, hexanoyl, or heptanoyl; $C_{1-8}$alkoxycarbonyl can be methoxycarbonyl, ethoxycarbonyl, propoxycarbonyl, isopropoxycarbonyl, butoxycarbonyl, pentoxycarbonyl, hexyloxycarbonyl, heptyloxycarbonyl, or octyloxycarbonyl; and $C_{1-8}$alkanoyloxy can be acetyloxy, propanoyloxy, butanoyloxy, isobutanoyloxy, pentanoyloxy, hexanoyloxy, heptanoyloxy, or octanoyloxy.

A specific value for $R^1$ is aryl or substituted aryl.

A specific value for $R^1$ is heteroaryl or substituted heteroaryl.

A specific value for $R^1$ is heterocycle or substituted heterocycle.

A specific value for $R^1$ and $R^2$ together with the nitrogen to which they are attached form a heterocycle, substituted heterocycle, heteroaryl, or substituted heteroaryl, and $R^3$ is H, $C_{1-8}$alkyl, aryl($C_{1-8}$alkylene) or substituted aryl($C_{1-8}$alkylene).

A specific value for $R^1$ and $R^2$ together with the nitrogen to which they are attached is 1,2,3,4,5,6-hexahydroazepino[4,5-b]indol-9-yl.

A specific value for $R^2$ is $C_{1-8}$alkyl.

A specific value for $R^2$ is aryl($C_{1-8}$alkylene) or substituted aryl($C_{1-8}$alkylene).

A more specific value for $R^2$ is H.

A specific value for $R^1$, $R^2$ and the nitrogen to which they are attached is a heterocyclic ring.

A specific value for $R^3$ is $C_{1-8}$alkyl.

A specific value for $R^3$ s aryl($C_{1-8}$alkylene) or substituted aryl($C_{1-8}$alkylene).

A more specific value for $R^3$ is H.

A preferred compound of formula (I) is: tert-Butyl 9-{[({6-[(2-methyl-3-pyridinyl)oxy]-3-pyridinyl}amino)carbonyl]amino}-1,4,5,6-tetrahydroazepino[4,5-b]indole-3(2H)-carboxylate; N-(1,2,3,4,5,6-hexahydroazepino[4,5-b]indol-9-yl)-N'-{6-[(2-methyl-3-pyridinyl)oxy]-3-pyridinyl}urea; 6-Methyl-N-{6-[(2-methylpyridin-3-yl)oxy]pyridin-3-yl}-1,4,5,6-tetrahydroazepino[4,5-b]indole-3(2H)-carboxamide; N-{6-[(2-methylpyridin-3-yl)oxy]pyridin-3-yl}-3,4-dihydroquinoline-1(2H)-carboxamide; N-{6-[(2-methylpyridin-3-yl)oxy]pyridin-3-yl}-3,4-dihydroisoquinoline-2(1H)-carboxamide; 4-Benzyl-N-{6-[(2-methylpyridin-3-yl)oxy]pyridin-3-yl}piperazine-1-carboxamide; N-{6-[(2-methylpyridin-3-yl)oxy]pyridin-3-yl}-N'-(2-phenylethyl)urea; and N-{6-[(2-methylpyridin-3-yl)oxy]pyridin-3-yl}azepine-1-carboxamide Specifically, the invention also provides a method for treating anxiety, obesity, depression, schizophrenia, a stress-related disease such as a general anxiety disorder, panic disorder, a phobia, obsessive compulsive disorder, post-traumatic-stress syndrome, immune system depression, a stress-induced problem with the gastrointestinal or cardiovascular system, or sexual dysfunction in a mammal, for example a human, comprising administering a therapeutically effective amount of a compound of formula (I), or a pharmaceutically acceptable salt thereof to the mammal. The term treating includes prophylaxis treatment.

Specifically, the invention also provides a method of treating anxiety, obesity, depression, or a stress-related disease, comprising administering to a mammal, for example a human, in need of such treatment, a therapeutically effective amount of a compound of formula I or a pharmaceutically acceptable salt thereof.

Specifically, the invention also provides the use of a compound of formula I or a pharmaceutically acceptable salt thereof to prepare a medicament for treating or preventing anxiety, obesity, depression, schizophrenia, a stress-related disease, such as a general anxiety disorder, panic disorder, a phobia, obsessive compulsive disorder, post-traumatic-stress syndrome, immune system depression, a stress-induced problem with the gastrointestinal or cardiovascular system, or sexual dysfunction in a mammal, for example a human.

Specifically, the invention also provides the use of a compound of formula (I) or a pharmaceutically acceptable salt thereof to prepare a medicament for treating or preventing anxiety, obesity, depression, or a stress-related disease in a mammal , for example a human.

The invention also provides processes and intermediates useful for preparing compounds of formula (I). For example, an intermediate useful for preparing a compound of formula (I) is a corresponding compound of formula (I) wherein $R^1$ is a suitable amine protecting group. Thus, the invention provides a compound of formula I wherein $R^1$ is a suitable amine protecting group.

Additionally, an intermediate useful for preparing a compound of formula (I) is a corresponding compound of formula (I) wherein $R^2$ is a suitable amine protecting group. Thus, the invention provides a compound of formula I wherein $R^2$ is a suitable amine protecting group.

Additionally, an intermediate useful for preparing a compound of formula (I) is a corresponding compound of formula (I) wherein $R^1$ and $R^2$ are each independently a suitable amine protecting group. Thus, the invention provides a compound of formula I wherein $R^1$ and $R^2$ are each independently a suitable amine protecting group.

Suitable amine protecting groups, as well as methods for their preparation and removal are well known in the art, for example, see Greene, T. W.; Wutz, P. G. M. "Protecting Groups In Organic Synthesis" third edition, 1999, New York, John Wiley & sons, Inc. Preferred protecting groups include benzyloxycarbonyl (CBZ) and benzoyl.

The invention also provides novel intermediate compounds that are useful in preparing compounds of formula (I), for example, the formulas as shown in preparative Schemes below.

The invention also provides intermediate salts that are useful for preparing or purifying compounds of formula (I). Suitable methods for preparing salts are known in the art and are disclosed herein. As will be apparent to one skilled in the art, such salts can be converted to the corresponding free-base or to another salt using known methods.

Compounds of the invention can generally be prepared using the synthetic routes illustrated in the Charts indicated below. Starting materials can be prepared by procedures described in these charts or by procedures that would be well known to one of ordinary skill in organic chemistry. The variables used in the charts are as defined below or as in the claims. The following describes the preparation of compounds of the present invention.

Preparation of compound 2 is depicted in Scheme A. The azepinoindole 1 was obtained by adopting the process described in *J. Org. Chem.*, Vol. 33, pp 3187-95 (1968). The nitro compound 1 is reduced with zinc dust in the presence of calcium chloride in 78% ethanol to form the amino compound 2. The other amines used in this invention are purchased from commercial resources.

Compounds of Formula I can be prepared by the reactions outlined in Scheme B. The substituted aryl amine 3 ($R^3$ is H) can be obtained by adopting the process described in *J. Med. Chem.*, Vol. 40, pp 3494-3496 (1997). When $R^3$ is other than H, for example $R^3$ is alkyl, the secondary amine can be obtained from the primary amine precursor by reductive amination using an aldehyde and a reducing agent such as sodium cyanoborohydride. The amine 3 can react with phenyl chloroformate (4) in the presence of triethylamine in dichloromethane to generate the carbamate 5. The reaction of carbamate 5 with the amine 6 in DMF in the presence of triethylamine thus leads to the formation of the urea formula I.

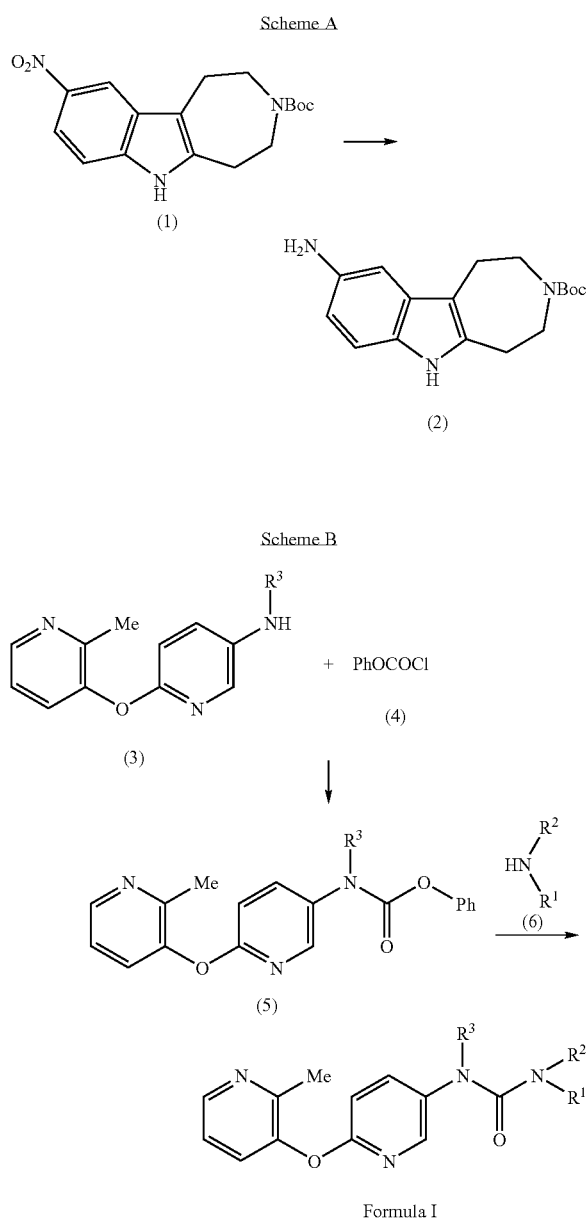

In some embodiments, the compounds are isotopically-labeled compounds. Isotopically-labeled compounds are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3$H, $^{11}$C, $^{14}$C, $^{13}$N, $^{15}$O, $^{18}$F, $^{99m}$Tc, $^{123}$I, and $^{125}$I. Compounds of the present invention and pharmaceutically acceptable salts and prodrugs of said compounds that contain the aforementioned isotopes and/or other isotopes of other atoms are within the scope of the invention. Isotopically-labeled compounds of the present invention are useful in drug and/or substrate tissue distribution and target occupancy assays. For example, isotopically labeled compounds are particularly useful in SPECT (single photon emission computed tomography) and in PET (positron emission tomography).

Single-photon emission computed tomography (SPECT), acquires information on the concentration of isotopically labeled compounds introduced to a mammal's body. SPECT dates from the early 1960's, when the idea of emission traverse section tomography was introduced by D. E. Kuhl and R. Q. Edwards prior to either PET, x-ray CT, or MRI. In general, SPECT requires isotopes that decay by electron capture and/or gamma emission. Example of viable SPECT isotopes include, but are not limited to, 123-iodine ($^{123}$I) and 99m-technetium ($^{99m}$Tc). Subjects are injected with a radioactively labeled agent, typically at tracer doses. The nuclear decay resulting in the emission of a single gamma ray which passes through the tissue and is measured externally with a SPECT camera. The uptake of radioactivity reconstructed by computers as a tomogram shows tissue distribution in cross-sectional images.

Positron emission tomography (PET) is a technique for measuring the concentrations of positron-emitting isotopes within the tissues. Like SPECT, these measurements are, typically, made using PET cameras outside of the living subjects. PET can be broken down into several steps including, but not limited to, synthesizing a compound to include a positron-emitting isotope; administering the isotopically labeled compound to a mammal; and imaging the distribution of the positron activity as a function of time by emission tomography. PET is described, for example, by Alavi et al. in Positron Emission Tomography published by Alan R. Liss, Inc. in 1985.

Positron-emitting isotopes used in PET include, but are not limited to, Carbon-11, Nitrogen-13, Oxygen-15, and Fluorine-18. In general, positron-emitting isotopes should have short half-lives to help minimize the long term radiation exposure that a patient receives from high dosages required during PET imaging.

In certain instances, PET imaging can be used to measure the binding kinetics of compounds of this invention with 5-HT$_{2C}$ serotonin receptors. For example, administering an isotopically labeled compound of the invention that penetrates into the body and binds to a 5-HT$_{2C}$ serotonin receptor creates a baseline PET signal which can be monitored while administering a second, different, non-isotopically labeled compound. The baseline PET signal will decrease as the non-isotopically labeled compound competes for the binding to the 5-HT$_{2C}$ serotonin receptor.

In general, compounds of formula I that are useful in performing PET or SPECT are those which penetrate the blood-brain barrier, exhibit high selectivity and modest affinity to 5-HT$_{2C}$ serotonin receptors, and are eventually metabolized. Compounds that are non-selective or those that exhibit excessive or small affinity for 5-HT$_{2C}$ serotonin receptors are, generally, not useful in studying brain receptor binding kinetics with respect to 5-HT$_{2C}$ serotonin receptors. Compounds that are not metabolized may harm the patient.

In other embodiments, nuclear magnetic resonance spectroscopy (NRS) imaging can be used to detect the overall concentration of a compound or fragment thereof containing nuclei with a specific spin. In general, the isotopes useful in NMR imaging include, but are not limited to, hydrogen-1, carbon-13, phosphorus-31, and fluorine-19. For instance, compounds containing $^{19}$F are useful in conducting NMR imaging.

Further, substitution with heavier isotopes such as deuterium, i.e., $^2$H, can afford certain therapeutic advantages resulting from greater metabolic stability, for example increased in vivo half-life or reduced dosage requirements and, hence, maybe preferred in some circumstances.

Compounds of formula (I) can be labeled using techniques which are well known in the art. For example, a radioisotope can be incorporated into the compound or appended to the compound of formula (I) using techniques well known in the art. For example, see Arthur Murry III, D. Lloyd Williams; *Organic Synthesis with Isotopes*, vol. I and II, Interscience Publishers Inc., N.Y. (1958) and Melvin Calvin et al. *Isotopic Carbon* John Wiley and Sons Inc., N.Y. (1949). Any radioisotope capable of being detected can be employed as a label. For example, suitable radioisotopes include: carbon-11, fluorine-18, fluorine-19, iodine-123 and iodine-125. Preferably, a compound of formula (I) may be labeled by appending one or more radioisotopes of a halogen (e.g. iodine-123) to an aromatic ring, or by alkylating a nitrogen of a compound of formula (I) with a group comprising a phenyl group bearing a radioisotope.

Isotopically labeled compounds of Formula I of this invention can also be prepared by carrying out the synthetic procedures described above by substituting an isotopically labeled reagent for a non-isotopically labeled reagent.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, carbonate salts, and the like salts. Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of the present invention can conveniently be administered in a pharmaceutical composition containing the compound in combination with a suitable excipient. Such pharmaceutical compositions can be prepared by methods and contain excipients which are well known in the art. A generally recognized compendium of such methods and ingredients is Remington's Pharmaceutical Sciences by E. W. Martin (Mark Publ. Co., 15th Ed., 1975). The compounds and compositions of the present invention can be administered parenterally, for example, by intravenous, intraperitoneal or intramuscular injection, topically, orally, or rectally.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol, for example, glycerol, propylene glycol, liquid polyethylene glycols, and the like; vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula (I) can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing about 0.05 mg to about 500 mg, conveniently about 0.1 mg to about 250 mg, most conveniently, about 1 mg to about 150 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compositions can conveniently be administered orally, sublingually, transdermally, or parenterally at dose levels of about 0.01 to about 150 mg/kg, preferably about 0.1 to about 50 mg/kg, and more preferably about 0.1 to about 10 mg/kg of mammal body weight.

For parenternal administration the compounds are presented in aqueous solution in a concentration of from about 0.1 to about 10%, more preferably about 0.1 to about 7%. The solution may contain other ingredients, such as emulsifiers, antioxidants or buffers.

The exact regimen for administration of the compounds and compositions disclosed herein will necessarily be dependent upon the needs of the individual subject being treated, the type of treatment and, of course, the judgment of the attending practitioner.

The ability of a compound of the invention to act as a 5-HT receptor agonist or antagonist can also be determined using in vitro and in vivo assays that are known in the art. The invention provides compounds of formula (I) that act as either agonists or as antagonists of one or more 5-HT receptor subtypes. The compounds exemplified herein are 5-HT receptor ligands, which typically displace a radio-labeled test ligand from one or more 5-HT receptor subtype at a concentration of, for example, about 1 micromolar (μM).

The procedures used for testing such displacement are well known and would be readily available to one skilled in the art. See for example, L. W. Fitzgerald et al., Mol. Pharmacol, 2000, 57, 1, 75-81; and D. B. Wainscott, et al., J. Pharmacol Exp Ther, 1996, 276, 2, 720-727.

PREPARATION 1

Preparation of tert-butyl 9-amino-1,4,5,6-tetrahydroazepino[4,5-b]indole-3(2H)-carboxylate

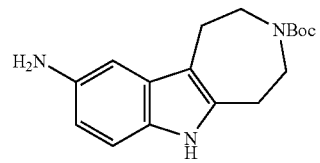

A mixture of tert-butyl 9-nitro-1,4,5,6-tetrahydroazepino[4,5-b]indole-3(2H)-carboxylate (0.25 g, 0.75 mmol), zinc (1.48 g, 22.6 mmol) and calcium chloride (0.04 g, 0.38 mmol) in 78% ethanol (7.5 mL) was refluxed for 2 h and filtered hot. The filtrate was concentrated in vacuo to dryness to give 0.22 g (99%) of solid as the desired product: MS (EI) m/z 302 (MH+).

EXAMPLE 1 tert-Butyl 9-{[({6-[(2-methyl-3-pyridinyl)oxy]-3-pyridinyl}amino)carbonyl]amino}-1,4,5,6-tetrahydroazepino[4,5-b]indole-3(2H)-carboxylate

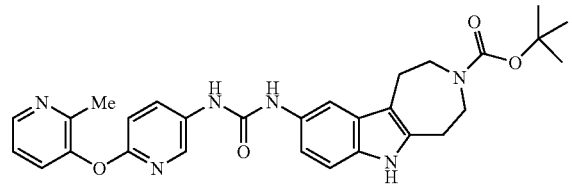

To a solution of phenyl chloroformate (0.14 mL, 0.18 g, 1.13 mmol) in dichloromethane (4.0 mL) was added the solution of 6-[(2-methylpyridin-3-yl)oxy]pyridin-3-amine (0.15 g, 0.75 mmol) and triethylamine (0.16 mL, 0.11 g, 1.13 mmol) in dichloromethane (4.0 mL) dropwise at −20° C. The resulting solution was stirred at −20° C. for 1 h and warmed to room temperature. The mixture was washed with sodium bicarbonate solution and dried with magnesium sulfate. After filtration, the filtrate was concentrated in vacuo to dryness. The residue was dissolved in DMF (4.0 mL). To this solution was added the solution of tert-butyl 9-amino-1,4,5,6-tetrahydroazepino[4,5-b]indole-3(2H)-carboxylate (0.23 g, 0.75 mmol) and triethylamine (0.12 mL, 0.084 g, 0.83 mmol) in DMF (4.2 mL). The resulting mixture was heated at 100° C. for 1 h. After cooling to room temperature, water (10 mL) and ethyl acetate (10 mL) were added and separated. The aqueous solution was extracted three times with ethyl acetate. The ethyl acetate solution was dried with magnesium sulfate and filtered. The filtrate was concentrated in vacuo to dryness and the residue was subjected to column chromatography (EtOAc) to give 0.33 g (83%) of light gray solid of Example 1: mp 173-175° C.; IR (KBr)

3327, 3296, 2976, 2916, 1690, 1667, 1639, 1592, 1551, 1475, 1448, 1420, 1376, 1368, 1350, 1330, 1315, 1288, 1265, 1247, 1238, 1221, 1169, 1111, 754 cm$^{-1}$; $^1$H NMR (300 MHz, CDCl$_3$) δ 8.44 (br, 1H), 8.36 (br, 1H), 8.30 (br, 1H), 8.02-7.96 (m, 1H), 7.81 (br, 1H), 7.65 (br, 1H), 7.48 (br, 1H), 7.30-7.22 (m, 2H), 7.13-7.02 (m, 2H), 6.83-6.80 (d, J=8.7 Hz, 1H), 3.58 (br, 4H), 2.83 (br, 4H), 2.39 (s, 3H), 1.47 (s, 9H); MS (EI) m/z 529 (MH$^+$); HRMS (FAB) cacld. for C$_{29}$H$_{32}$N$_6$O$_4$+H: 529.2563, found: 529.2550; Anal. Calcd. for C$_{29}$H$_{32}$N$_6$O$_4$: C, 65.89; H, 6.10; N, 15.90. Found: C, 65.89; H, 6.23; N, 15.63.

EXAMPLE 2

N-(1,2,3,4,5,6-Hexahydroazepino[4,5-b]indol-9-yl)-N'-{6-[(2-methyl-3-pyridinyl)oxy]-3-pyridinyl}urea

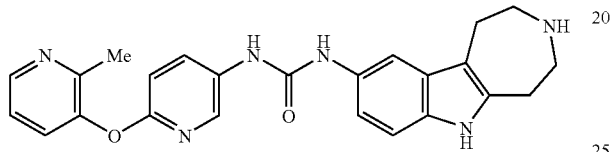

To a solution of tert-butyl 9-{[({6-[(2-methyl-3-pyridinyl)oxy]-3-pyridinyl}amino)carbonyl]amino}-1,4,5,6-tetrahydroazepino[4,5-b]indole-3(2H)-carboxylate (0.154 g, 0.291 mmol) in dichloromethane (3.0 mL) was added trifluoroacetic acid (0.75 mL) dropwise. After stirring at room temperature for 1 h, the solvent was removed in vacuo to dryness. The residue was partitioned in chloroform (10.0 mL) and sodium hydroxide solution (1N, 10.0 mL). The solidified material was filtered off and collected to give 0.12 g (96%) of Example 2: mp 205-207° C.; IR (KBr) 3288, 1629, 1554, 1478, 1450, 1374, 1269, 1228, 1178, 1122 cm$^{-1}$; $^1$H NMR (300 MHz, DMSO-d$_6$) δ 8.28 (d, J=2.3 Hz, 1H), 8.13 (d, J=2.0 Hz, 1H), 8.03 (dd, J=7.8, 2.3 Hz, 1H), 7.47-7.41 (m, 2H), 7.30-7.21 (m, 1H), 7.10-6.91 (m, 3H), 5.73 (s, 1H), 2.86-2.48 (m, 8H), 2.30 (s, 3H); MS m/z 429 (MH$^+$); HRMS (FAB) cacld. for C$_{24}$H$_{24}$N$_6$O$_2$+H: 429.2039, found: 429.2043; Anal. Calcd. for C$_{24}$H$_{24}$N$_6$O$_2$+0.5H$_2$O: C, 65.89; H, 5.76; N, 19.21. Found: C, 65.29; H, 5.70; N, 18.99.

EXAMPLE 3

6-Methyl-N-{6-[(2-methylpyridin-3-yl)oxy]pyridin-3-yl}-1,4,5,6-tetrahydroazepino[4,5-b]indole-3(2H)-carboxamide

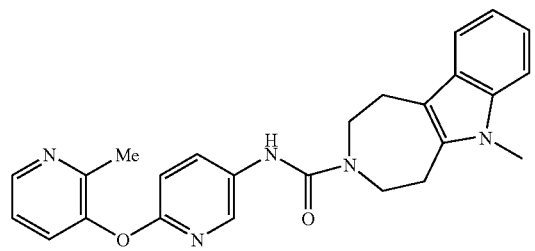

Following the procedure of Example 1, using 6-methyl-1,2,3,4,5,6-hexahydroazepino[4,5-b]indole and 6-[(2-methylpyridin-3-yl)oxy]pyridin-3-amine as the starting materials, Example 3 was prepared as a colorless solid (53%): mp 159-160° C.; IR (KBr) 3313, 2931, 1635, 1607, 1590, 1521, 1477, 1438, 1407, 1380, 1368, 1353, 1342, 1318, 1269, 1230, 1204, 1180, 1163, 1129, 1112, 829, 804, 758, 744 cm$^{-1}$; $^1$H NMR (300 MHz, CDCl$_3$) δ 8.34 (br, 1H), 8.00 (dd, J=8.8, 2.7 Hz, 1H), 7.95 (d, J=2.6 Hz, 1H), 7.47 (d, J=7.7 Hz, 1H), 7.35 (d, J=6.9 Hz, 1H), 7.27-7.25 (m, 1H), 7.21-7.08 (m, 3H), 6.91 (d, J=8.8 Hz, 1H), 6.45 (s, 1H), 4.03 (t, J=5.5 Hz, 2H), 3.82 (t, J=5.5 Hz, 2H), 3.65 (s, 3H), 3.20 (t, J=5.7 Hz, 2H), 3.14 (t, J=5.6 Hz, 2H), 2.44 (s, 3H); MS m/z 428 (MH$^+$); HRMS (FAB) cacld. for C$_{25}$H$_{25}$N$_5$O$_2$+H: 428.2086, found: 428.2082; Anal. Calcd. for C$_{25}$H$_{25}$N$_5$O$_2$: C, 70.24; H, 5.89; N, 16.38. Found: C, 70.11; H, 5.97; N, 16.29.

EXAMPLE 4

N-{6-[(2-Methylpyridin-3-yl)oxy]pyridin-3-yl}-3,4-dihydroquinoline-1(2H)-carboxamide

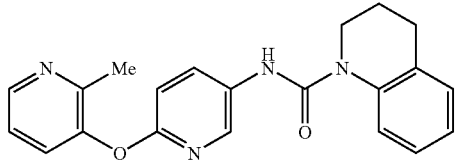

EXAMPLE 4

Following the procedure of Example 1, using 1,2,3,4-tetrahydroquinoline and 6-[(2-methylpyridin-3-yl)oxy]pyridin-3-amine as the starting materials, Example 4 was prepared as a beige solid (33%): mp 104-107° C.; IR (diffuse reflectance) 2399, 2350, 2338, 2276, 2220, 1646, 1530, 1485, 1446, 1292, 1272, 1265, 1237, 1228, 1165 cm$^{-1}$; $^1$H NMR (400 MHz, CDCl$_3$) δ 8.35 (dd, J=1, 5 Hz, 1H), 8.04 (dd, J=3, 9 Hz, 1H), 7.92 (d, J=3 Hz, 1H), 7.35-7.31 (m, 2H), 7.25-7.22 (m, 1H), 7.18-7.11 (m, 2H), 7.00 (s, 1H), 6.92 (d, J=9 Hz, 1H), 3.83 (t, J=6 Hz, 2H), 2.80 (t, J=7 Hz, 2H), 2.43 (s, 3H), 2.04-2.78 (m, 2H); $^{13}$C NMR (100 MHz, CDCl$_3$) δ 158.8, 153.9, 152.0, 149.0, 145.2, 138.5, 138.4, 133.0, 132.4, 131.4, 129.9, 128.6, 127.0, 125.1, 122.9, 122.0, 111.2, 43.5, 27.0, 24.0, 19.6; MS (EI) m/z 360 (M$^+$); Anal. Calcd for C$_{21}$H$_{20}$N$_4$O$_2$: C, 69.98; H, 5.59; N, 15.55. Found: C, 69.76; H, 5.59; N, 15.30.

EXAMPLE 5

N-{6-[(2-Methylpyridin-3-yl)oxy]pyridin-3-yl}-3,4-dihydroisoquinoline-2(1H)-carboxamide

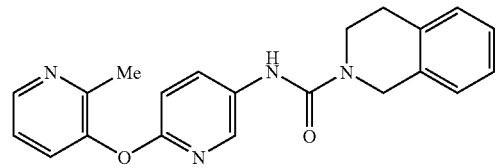

Following the procedure of Example 1, using 1,2,3,4-tetrahydroisoquinoline and 6-[(2-methylpyridin-3-yl)oxy]pyridin-3-amine as the starting materials, Example 5 was prepared as a clear oil (70%): IR (diffuse reflectance) 1916, 1662, 1645, 1531, 1482, 1446, 1414, 1393, 1380, 1372, 1246, 1229, 1197, 1167, 749 cm$^{-1}$; $^1$H NMR (CDCl$_3$) δ 8.37 (dd, J=1, 5 Hz, 1H), 8.03 (dd, J=3, 9 Hz, 1H), 7.99 (d, J=3 Hz, 1H), 7.38 (dd, J=1, 8 Hz, 1H), 7.26-7.17 (m, 5H), 6.93 (d, J=9 Hz, 1H), 6.57 (s, 1H), 4.70 (s, 2H), 3.76 (t, J=6 Hz, 2H), 2.96 (t, J=6 Hz, 2H), 2.45 (s, 3H); $^{13}$C NMR (100 MHz, CDCl$_3$) δ 158.8, 155.1, 152.0, 148.9, 145.1, 139.1, 134.8, 133.6, 132.9, 131.8, 129.3, 128.8, 128.4, 126.9, 126.6, 126.3, 111.1, 45.8, 41.6, 29.0, 19.5; MS (EI) m/z 360 (M$^+$); HRMS (FAB) calcd for C$_{21}$H$_{20}$N$_4$O$_2$+H 361.1664, found 361.1669.

EXAMPLE 6

4-Benzyl-N-{6-[(2-methylpyridin-3-yl)oxy]pyridin-3-yl}piperazine-1-carboxamide

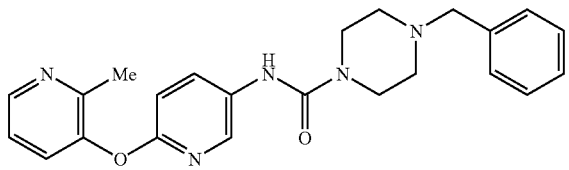

Following the procedure of Example 1, using benzyl piperazine and 6-[(2-methylpyridin-3-yl)oxy]pyridin-3-amine as the starting materials, Example 6 was prepared as a clear oil (63%): IR (diffuse reflectance) 2499, 1948, 1662, 1639, 1531, 1481, 1447, 1415, 1297, 1247, 1230, 1210, 1173, 1000, 741 cm$^{-1}$; $^1$H NMR (400 MHz, CDCl$_3$) δ 8.33 (dd, J=1, 5 Hz, 1H), 7.95 (dd, J=3, 9 Hz, 1H), 7.89 (d, J=3 Hz, 1H), 7.35-7.25 (m, 6H), 7.16 (dd, J=5, 8 Hz, 1H), 6.88 (d, J=9 Hz, 1H), 6.72 (s, 1H), 3.54-3.49 (m, 6H), 2.49-2.46 (m, 4H), 2.41 (s, 3H); $^{13}$C NMR (100 MHz, CDCl$_3$) δ 158.8, 155.1, 152.0, 149.0, 145.1, 139.0, 137.5, 133.5, 131.7, 129.1, 128.8, 128.4, 127.3, 122.1, 111.1, 62.9, 52.6, 44.1, 19.5; MS (EI) m/z 403 (M$^+$); HRMS (FAB) calcd for C$_{23}$H$_{25}$N$_5$O$_2$+H 404.2086, found 404.2077.

EXAMPLE 7

N-{6-[(2-Methylpyridin-3-yl)oxy]pyridin-3-yl}-N'-(2-phenylethyl)urea

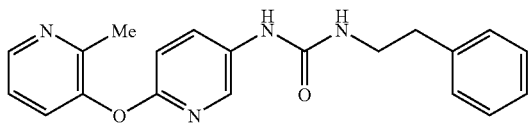

Following the procedure of Example 1, using phenethylamine and 6-[(2-methylpyridin-3-yl)oxy]pyridin-3-amine as the starting materials, Example 7 was prepared as a colorless solid (85%): mp 136-138° C.; IR (diffuse reflectance) 3347, 3302, 1634, 1608, 1587, 1563, 1525, 1484, 1453, 1431, 1377, 1295, 1279, 1234, 1175, 1114, 830, 821, 756, 722, 702 cm$^{-1}$; $^1$H NMR (400 MHz, CDCl$_3$) δ 8.22 (br, 1H), 8.03 (dd, J=9.0, 2.9 Hz, 1H), 7.65 (d, J=2.8 Hz, 1H), 7.32 (dd, J=8.0, 1.3 Hz, 1H), 7.28-7.24 (m, 2H), 7.21-7.13 (m, 5H), 6.87 (d, J=8.9 Hz, 1H), 5.36 (t, J=5.6 Hz, 1H), 3.54-3.49 (m, 2H), 2.83 (t, J=6.8 Hz, 2H), 2.36 (s, 3H); $^{13}$C NMR (100 MHz, CDCl$_3$) δ 158.6, 155.8, 152.4, 149.2, 145.0, 138.9, 138.1, 132.4, 131.9, 129.5, 128.8, 128.7, 126.5, 122.4, 111.1, 41.4, 36.2, 19.4; MS (EI) m/z 348 (M$^+$); HRMS (FAB) calcd for C$_{20}$H$_{20}$N$_4$O$_2$+H 349.1664, found 349.1657; Anal. Calcd for C$_{20}$H$_{20}$N$_4$O$_2$+0.5H$_2$O: C, 67.21; H, 5.92; N, 15.68. Found: C, 67.84; H, 5.79; N, 15.77.

EXAMPLE 8

N-{6-[(2-Methylpyridin-3-yl)oxy]pyridin-3-yl}azepane-1-carboxamide

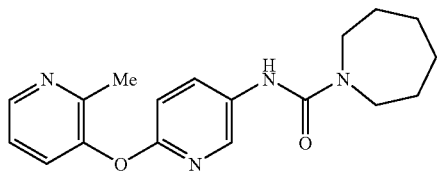

Following the procedure of Example 1, using hexamethyleneimine and 6-[(2-methylpyridin-3-yl)oxy]pyridin-3-amine as the starting materials, Example 8 was prepared as a clear oil (54%): IR (liq.) 2929, 2128, 1918, 1640, 1607, 1592, 1527, 1481, 1447, 1411, 1370, 1249, 1234, 1205, 1174 cm$^{-1}$; $^1$H NMR (400 MHz, CDCl$_3$) δ 8.35-8.33 (m, 1H), 8.03 (dd, J=3, 9 Hz, 1H), 7.94 (d, J=3 Hz, 1H), 7.34 (dd, J=1, 8 Hz, 1H), 7.19-7.15 (m, 1H), 6.89 (d, J=9 Hz, 1H), 6.36 (s, 1H), 3.52-3.49 (m, 5H), 2.44 (s, 3H), 1.81-1.76 (m, 2H), 1.63-1.60 (m, 5H); $^{13}$C NMR (100 MHz, CDCl$_3$) δ 158.7, 155.2, 151.9, 149.1, 145.1, 138.9, 133.4, 132.0, 128.6, 122.0, 111.1, 46.7, 28.5, 27.3, 14.4; MS (EI) m/z 326 (M$^+$); HRMS (FAB) calcd for C$_{18}$H$_{22}$N$_4$O$_2$+H 327.1821, found 327.1830.

The invention has been described with reference to various specific and preferred embodiments and techniques. However, it should be understood that many variations and modifications may be made while remaining within the spirit and scope of the invention.

What is claimed is:

1. A compound selected from the group of:
tert-Butyl 9-{[({6-[(2-methyl-3-pyridinyl)oxy]-3-pyridinyl}amino)carbonyl]amino}-1,4,5,6-tetrahydroazepino[4,5-b]indole-3(2H)-carboxylate;
N-(1,2,3,4,5,6-Hexahydroazepino[4,5-b]indol-9-yl)-N'-{6-[(2-methyl-3-pyridinyl)oxy]-3-pyridinyl}urea;
6-Methyl-N-{6-[(2-methylpyridin-3-yl)oxy]pyridin-3-yl}-1,4,5,6-tetrahydroazepino[4,5-b]indole-3(2H)-carboxamide;
N-{6-[(2-Methylpyridin-3-yl)oxy]pyridin-3-yl}-3,4-dihydroquinoline-1(2H)-carboxamide;
N-{6-[(2-Methylpyridin-3-yl)oxy]pyridin-3-yl}-3,4-dihydroisoquinoline-2(1H)-carboxamide;
4-Benzyl-N-{6-[(2-methylpyridin-3-yl)oxy]pyridin-3-yl}piperazine-1-carboxamide;
N-{6-[(2-Methylpyridin-3-yl)oxy]pyridin-3-yl}-N'-(2-phenylethyl)urea;
N-{6-[(2-Methylpyridin-3-yl)oxy]pyridin-3-yl}azepane-1-carboxamide;
or a pharmaceutically acceptable salt thereof.

2. A pharmaceutical composition comprising a compound of claim 1 and a pharmaceutically acceptable excipient.

* * * * *